(12) United States Patent
Kleih et al.

(10) Patent No.: US 10,383,681 B2
(45) Date of Patent: Aug. 20, 2019

(54) PROBE APPLICATOR

(71) Applicant: BOWA-electronic GmbH & Co. KG, Gomaringen (DE)

(72) Inventors: Joerg Kleih, Gomaringen (DE); Alexander Doppelstein, Bodelshausen (DE); Heinz Hluchy, Moessingen (DE)

(73) Assignee: BOWA-electronic GmbH & Co. KG (DE)

( * ) Notice: Subject to any disclaimer, the term of this patent is extended or adjusted under 35 U.S.C. 154(b) by 274 days.

(21) Appl. No.: 14/716,972

(22) Filed: May 20, 2015

(65) Prior Publication Data

US 2015/0335378 A1    Nov. 26, 2015

(30) Foreign Application Priority Data

May 20, 2014  (DE) .................. 10 2014 107 087

(51) Int. Cl.
  *A61B 18/14*  (2006.01)
  *A61B 17/00*  (2006.01)
  *A61B 18/00*  (2006.01)

(52) U.S. Cl.
  CPC ........ *A61B 18/1482* (2013.01); *A61B 18/149* (2013.01); *A61B 2017/00323* (2013.01); *A61B 2017/00336* (2013.01); *A61B 2017/00862* (2013.01); *A61B 2018/00196* (2013.01); *A61B 2018/00339* (2013.01); *A61B 2018/00625* (2013.01); *A61B 2018/142* (2013.01); *A61B 2018/1475* (2013.01)

(58) Field of Classification Search
  CPC .............. A61B 18/482; A61B 18/1492; A61B 2018/1475; A61B 2018/1497; A61B 2018/00196; A61B 2017/00292; A61B 2017/00336; A61N 1/0587; A61N 1/0529; A61N 1/0534
  See application file for complete search history.

(56) References Cited

U.S. PATENT DOCUMENTS

| | | |
|---|---|---|
| 5,098,441 A | 3/1992 | Wechler |
| 5,472,441 A | 12/1995 | Edwards et al. |
| 6,210,409 B1 | 4/2001 | Ellman |
| 6,231,571 B1 | 5/2001 | Ellman |
| 6,352,533 B1 | 3/2002 | Ellman |
| 7,101,370 B2 | 9/2006 | Garito et al. |

(Continued)

FOREIGN PATENT DOCUMENTS

| | | |
|---|---|---|
| CN | 202397597 | 8/2012 |
| DE | 60028863 | 11/2006 |
| EP | 1607061 | 12/2005 |

*Primary Examiner* — Tammie K Marlen
(74) *Attorney, Agent, or Firm* — Gerald E. Hespos; Michael J. Porco; Matthew T. Hespos

(57) ABSTRACT

A probe applicator (1) is provided for positioning a bipolar electrosurgical probe (2) that has a bendable distal end (5) with a tip that forms a bipolar electrode head (9) connected to two electrical conductors (7, 8). The probe (2) is arranged in a casing (6), and both the probe (2) and the casing (6) are longitudinally displaceable in a rigid shaft tube (3). The distal probe end (5) is pre-tensioned into a curved shape when the shaft tube end (17) is retracted. However, the probe end (5) is tensioned into an extended position by the surrounding end (17) of the shaft tube (3) when the shaft tube (3) is advanced. The second electrical conductor (8) is a flexible wire cable.

9 Claims, 5 Drawing Sheets

(56) References Cited

U.S. PATENT DOCUMENTS

| | | | |
|---|---|---|---|
| 7,610,104 B2* | 10/2009 | Kaplan | A61N 1/0587 607/115 |
| 8,430,888 B2* | 4/2013 | Malinowski | A61N 1/0529 606/129 |
| 9,399,130 B2* | 7/2016 | Bonde | A61B 17/3415 |
| 2005/0107779 A1 | 5/2005 | Ellman et al. | |
| 2008/0269740 A1* | 10/2008 | Bonde | A61B 17/3415 606/53 |
| 2014/0288384 A1* | 9/2014 | Mulrooney | A61B 5/04884 600/301 |

* cited by examiner

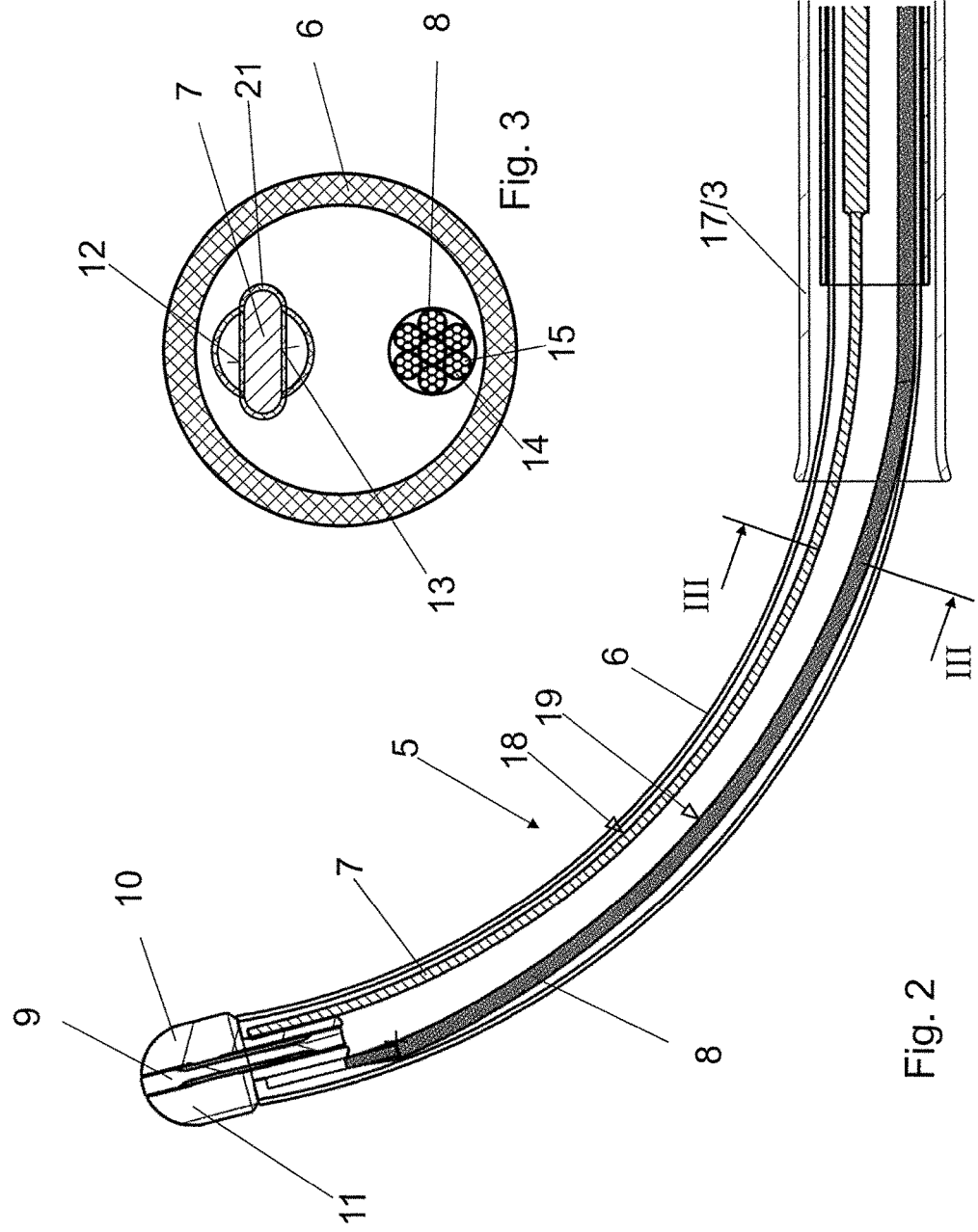

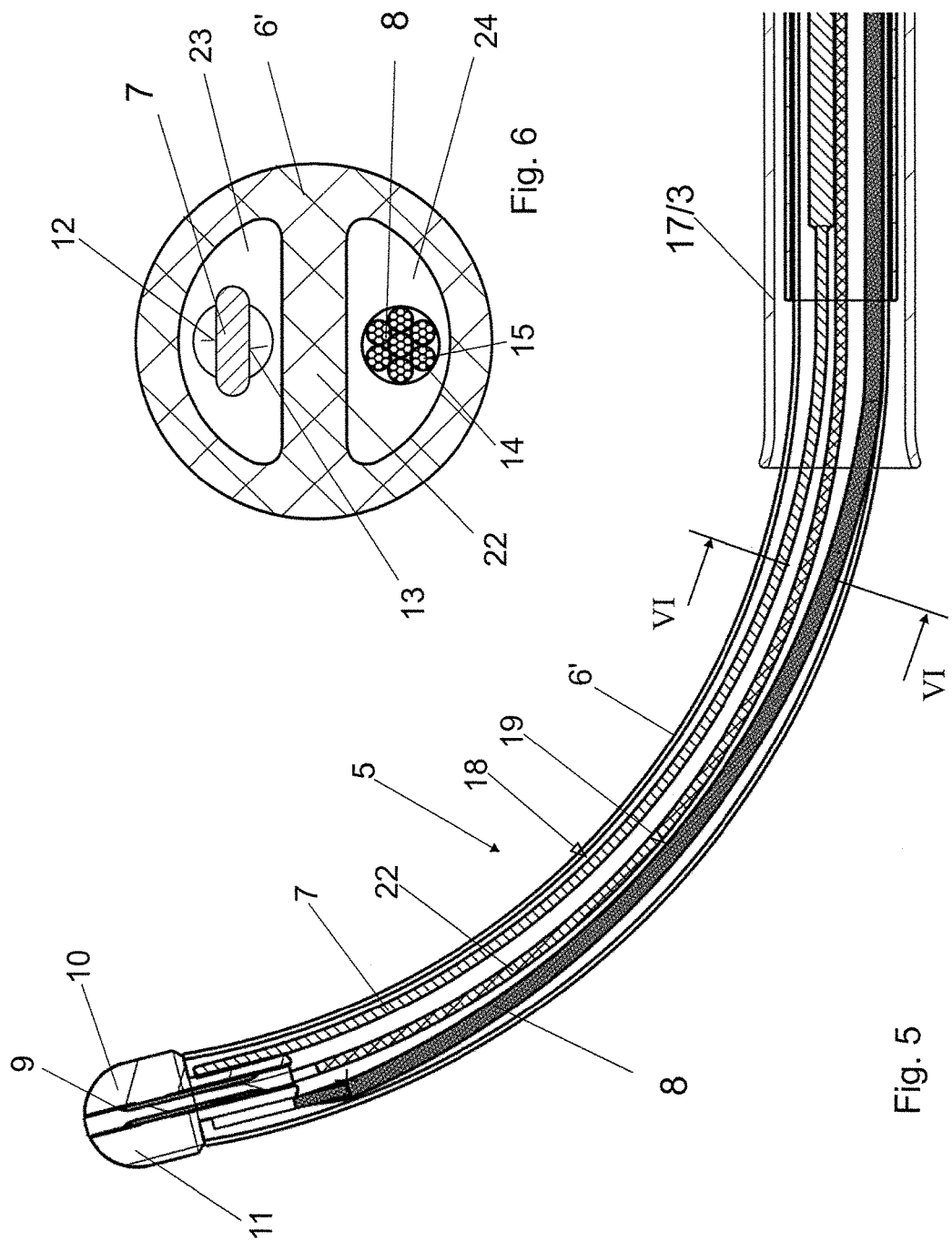

PROBE APPLICATOR

BACKGROUND

1. Field of the Invention

The invention relates to a probe applicator for positioning a bipolar electrosurgical probe having a bendable distal probe end that has a probe tip with a bipolar electrode head, which is connected to two electrical conductors housed in a flexible probe casing, and having a shaft tube in which the probe is housed, and a handpiece that allows the probe end to be flexed selectively.

2. Description of the Related Art

Probe applicators are used, for example, as bipolar vaporization probes (for percutaneous nucleus therapy) in minimally invasive surgery (MIS) procedures for treatment of herniated spinal disks.

A probe applicator for positioning a bipolar electrosurgical probe with a bendable distal probe end is known from EP 1 607 061 B1. The distal probe end has a probe tip with a bipolar electrode head, which is connected to two electrical conductors housed in a probe casing. The probe is longitudinally displaceable in a tube by means of a handpiece. The probe end can be flexed by using the handpiece. The distal end of the probe casing is pre-curved and when covered by the distal shaft tube end, is tensioned into an extended position.

The probe applicator disclosed in EP 1 607 061 B1 is disadvantageous in that the probe casing itself has a pre-curved form or tensioning. It is further disadvantageous that relatively high shear forces act on the outer conductor (electrode) when two conductors are arranged parallel to one another, especially with very pronounced curvature. Once the probe tip is brought into its extended, straight position, i.e. not deflected vis-à-vis its longitudinal axis, this results in compression of the outer electrode, which places stress on the outer electrode. Moreover, the relative motion between the probe and outer tube is hindered due to increased friction.

Furthermore, a similar probe applicator is known from DE 600 28 863 T2, in which the probe casing has a pre-tensioned, curved form. In this case, the probe casing is to be made of a material that can be pre-curved and has sufficient memory to maintain its pre-curved form when the probe casing and/or probe is extended outwards from the opposite-acting outer tube. This probe applicator also has the disadvantages described above.

The present invention seeks to simplify the design of the pre-tensioned curvature of the probe tip and to reduce the stress on the outer electrode, in particular, in the event of compression.

SUMMARY OF THE INVENTION

The invention relates to a probe applicator for positioning a bipolar electrosurgical probe with a bendable distal probe end having a probe tip with a bipolar electrode head that is connected to two electrical conductors arranged in a probe casing. The probe is arranged in a shaft tube. A handpiece is provided and makes it possible to flex the probe end. The shaft tube is of rigid design, and the shaft tube and the probe casing are longitudinally displaceable relative to one another. The distal end of the probe is pre-curved and is tensioned into an extended position when it is covered by the distal end of the shaft tube. The first electrical conductor has a directionally curved pre-tensioning in the region of the distal probe end which, when the shaft tube end is retracted, allows the free probe end of the flexible probe to be pressed into its curved, pre-flexed position and when the shaft tube is advanced, the probe end is tensioned into its extended position by the surrounding shaft tube end, and the second electrical conductor is designed as a flexible wire cable.

Since the curved pre-tensioning of the distal probe end is not accomplished through the probe casing, but rather through the first electrode, this significantly simplifies the pre-tensioning. By designing the outer electrode as a flexible wire cable, the compression of the electrode, which is necessary during straight extension, is considerably improved due to lower stress.

The first electrical conductor may be arranged in the inner position relative to the direction of bending while the second electrical conductor may be arranged in the outer position relative to the direction of bending. In the region of the curved pre-tensioning of the distal probe end, the first electrical conductor is designed to be flat, with two opposing side faces. At least in this region, the electrical conductor can be made of a tempered component, such as one made of stainless steel, which is given its pre-curved form by means of a rolling process, for example. The probe casing can be made of a flexible plastic.

The flexible wire cable may be made of a plurality of strands, each made of a plurality of wires. Such a wire cable can be especially easily compressed, since separation of the strands can occur. For example, the wire cable can be comprised of an odd number of strands, each with an odd number of wires. In this connection, a core can be formed in each case, around which a plurality of wires or strands is arranged.

The flexible probe casing may have a ring-shaped cross-section and at least one of the electrical conductors has an insulating cover. This has the advantage that the probe casing can be designed as a single tube and the two electrical conductors arranged parallel alongside one another in the casing are insulated from one another.

In principle, however, it is also possible for the cross-section of the flexible probe casing internally to have a contour that narrows in the middle, in which the electrical conductors are arranged at a distance from one another. This provides insulation in the form of air and makes it unnecessary for one of the two conductors to be insulated.

The flexible probe casing may have a separator wall that divides the lumen of the probe casing into two separate chambers, in which the electrical conductors are arranged. In this case as well, no insulation of the electrical conductors themselves is necessary. Accordingly, the probe casing is made of an electrically insulating plastic.

Additional features and advantages of the invention are evident from the following special description and the drawings.

BRIEF DESCRIPTION OF THE DRAWINGS

FIG. 2 is an enlarged cross-sectional view of the probe tip with the distal shaft tube end from FIG. 1.

FIG. 3 is an enlarged illustration of the probe tip from FIG. 2 along the line III-III.

FIG. 5 is an enlarged cross-sectional view of a probe tip of another probe applicator, corresponding to FIG. 2.

FIG. 6 is an enlarged cross-sectional view of the probe tip from FIG. 5 corresponding to the illustration in FIG. 3.

DETAILED DESCRIPTION

Figure 1:
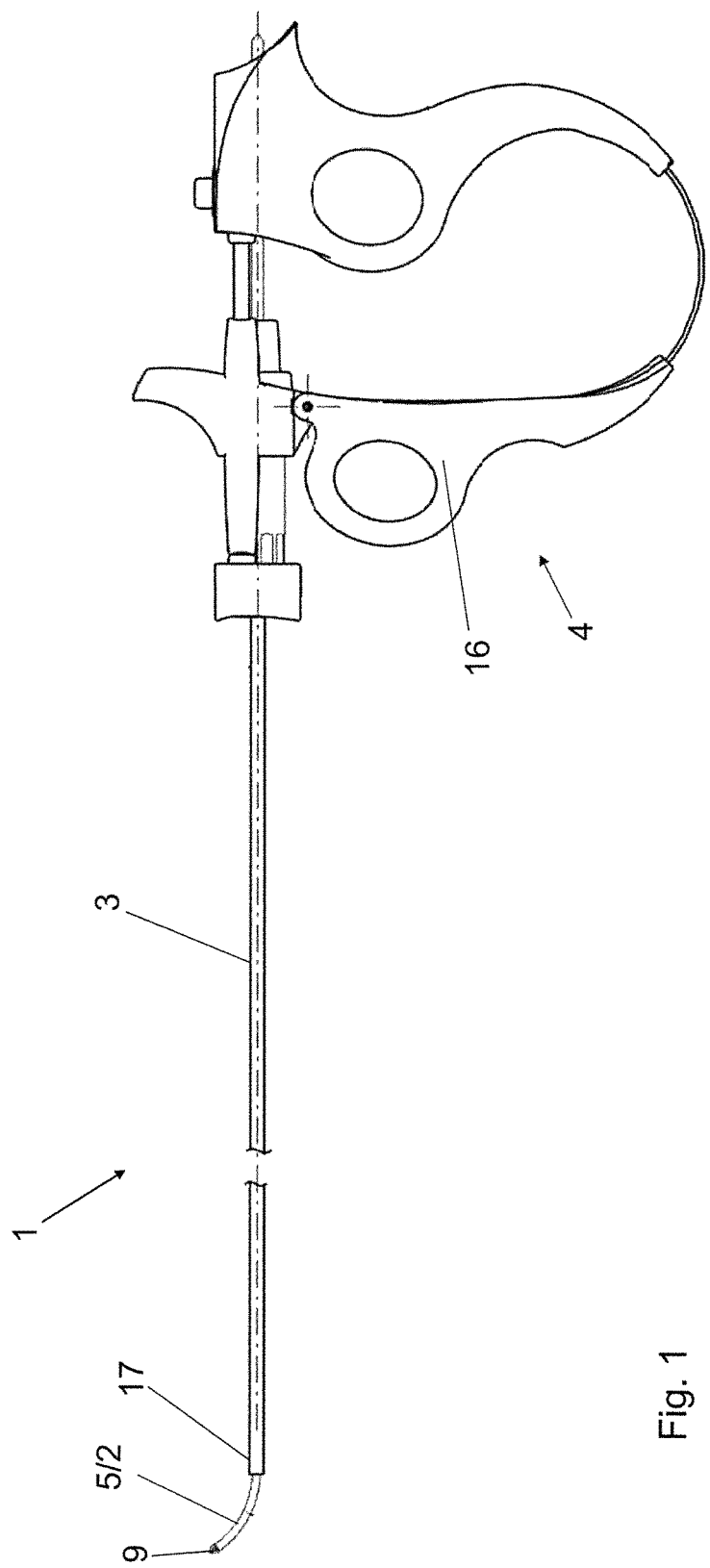
FIG. 1 is a lateral view of a probe applicator with extended and bent probe tip.

A probe applicator 1 in accordance with an embodiment of this disclosure includes a probe 2, a shaft tube 3 and a handpiece 4.

The probe 2 is designed as a bipolar electrosurgical probe with a bendable distal probe end 5. The probe has a flexible probe casing 6 made of plastic. Within the probe casing 6, a first electrical conductor 7 and a second electrical conductor 8 are arranged parallel to and at a distance from one another. At the distal probe end 5, a bipolar electrode head 9 with a first pole 10 and a second pole 11 is arranged, which centrally closes off the probe casing 6 and with whose poles 10, 11 the electrical conductors 7, 8 are connected.

In the region of the distal probe end 5, the first electrical conductor 8 is directionally pre-tensioned so that the free distal probe end 5 is pressed into its pre-curved, bent position. The first electrical conductor 7 is arranged flat, with two opposing side faces 12, 13 in the region of the curved pre-tensioning of the distal probe end 5. The necessary pre-tensioning can be imparted by a rolling process, for example.

The second electrical conductor 8 is designed as a flexible wire cable and consists of a plurality of strands 14. Each strand 14 itself consists of a plurality of wires 15. For example, the wire cable can be comprised of an odd number of strands 14, each with an odd number of wires 15.

Figure 4:
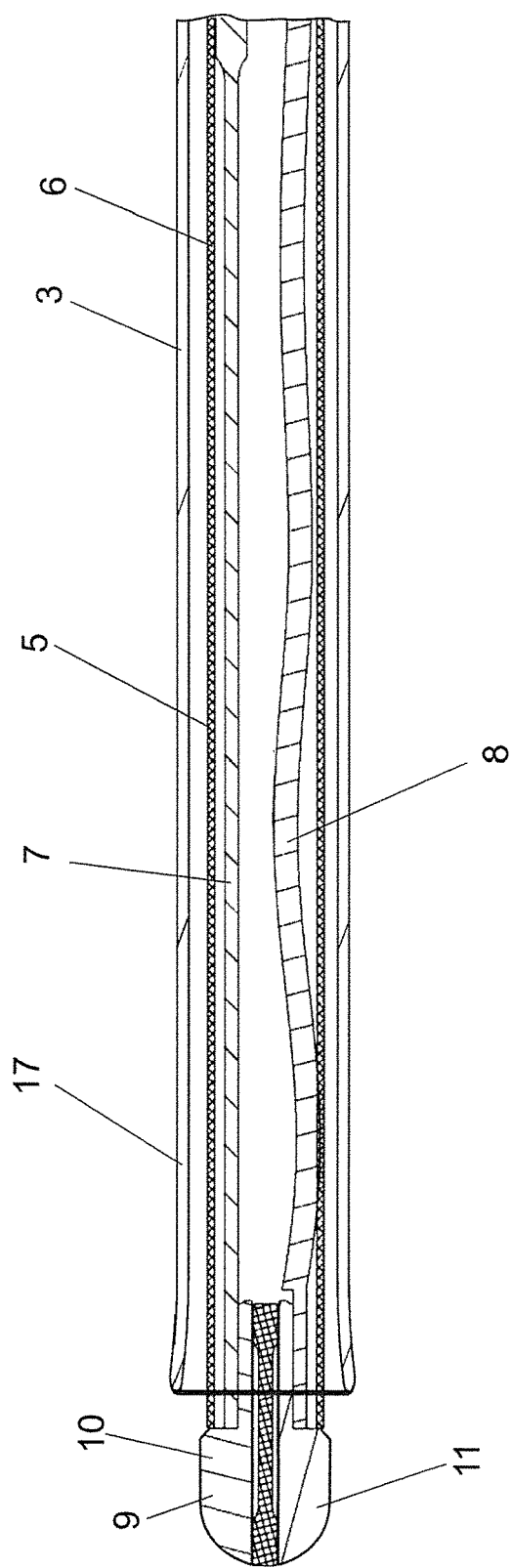
FIG. 4 is an enlarged illustration of the probe tip with the distal shaft tube in the advanced position, in which the shaft tube end covers the distal end of the probe tip.

The probe 2 with its probe casing 6 is arranged in the shaft tube 3 so as to be longitudinally displaceable. The probe 2 and shaft tube 3 are each connected to the handpiece 4, via the handle 16 of which it is possible to displace the probe 2 and the shaft tube 3 relative to each other in their longitudinal direction. When the distal shaft tube end 17 no longer covers the distal probe end 5, the distal probe end 5 is in its maximally curved position as a result of the pre-tensioning (see FIGS. 1, 2 and 5). When the distal probe end 5 is covered by the distal shaft tube end 17, the distal probe end 5 is in its non-curved, extended position (see FIG. 4).

The probe 2 has the first electrical conductor 7 on its inner side relative to the direction of bending, the conductor then being curved around the smaller inner radius 18. In the lumen on its outer side relative to the direction of bending, the probe 2 has the second electrical conductor 8, which is curved around the larger inner radius 19.

According to the exemplary embodiment from FIGS. 2 and 3, the cross-section of the flexible probe casing 6 is ring-shaped, i.e. the probe casing 6 has a ring-shaped wall 20, and the first electrical conductor 7 is provided with insulation 21.

According to the exemplary embodiment from FIGS. 5 and 6, the flexible probe casing 6' has a ring-shaped cross section and a centrally-arranged dividing wall 22 which divides the lumen of the probe casing 6' into two chambers, 23, 24, each of which accommodates an electrical conductor 7, 8, such that neither of the electrical conductors 7, 8 requires its own insulation.

Figure 7:
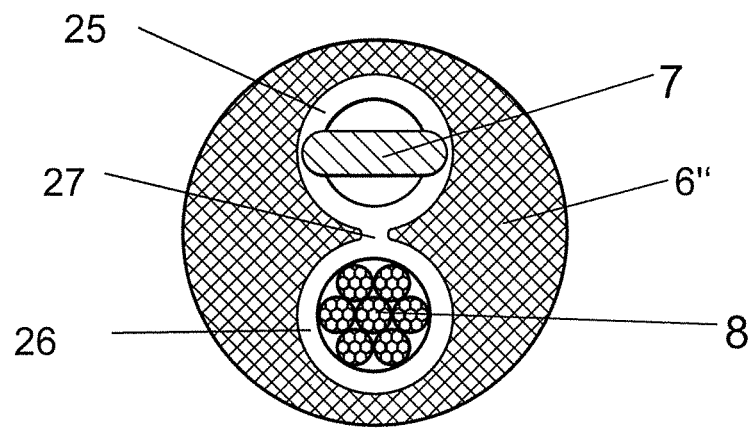
FIG. 7 is an enlarged cross-sectional view of another probe tip corresponding to the illustration in FIG. 3.
Figure 8:
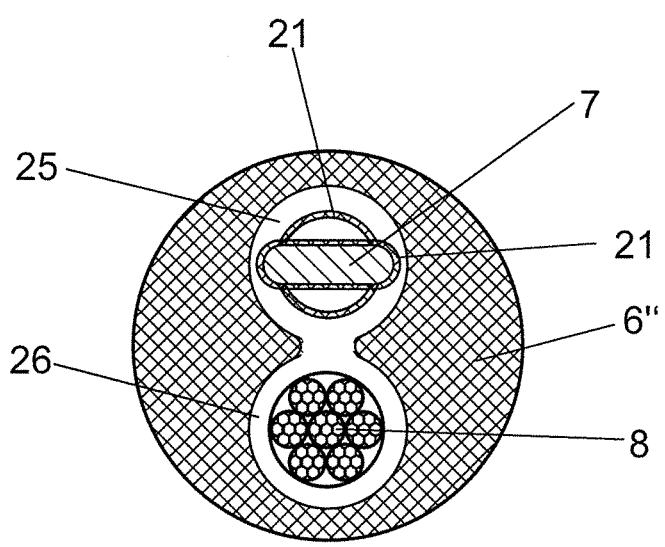
FIG. 8 is an enlarged cross-sectional view of another probe tip corresponding to the illustration in FIG. 3.

According to the exemplary embodiment from FIG. 7, the lumen of the probe casing 6" has two merging channels 25, 26, which are connected to one another, and which insulate the electrical conductors 7, 8 from one another by way of an intermediate air space 27. The design of the exemplary embodiment from FIG. 8 corresponds to FIG. 7, however the first electrical conductor has insulation 21.

The probe applicator 1 is placed at the operation site with the distal probe end 5 being covered by the distal shaft tube end 17, i.e. with the probe end 5 extended, not curved, and then actuation of the handle 16 causes the shaft tube 3 to be retracted relative to the probe 2, so that the distal probe end 5, which is no longer covered, is tensioned into its bent position.

Of course, the embodiments discussed in the special description and shown in the figures are merely exemplary embodiments of the present invention. The present disclosure puts a broad range of possible variations at the disposal of a person skilled in the art.

LIST OF REFERENCE NUMBERS

1 Probe applicator
2 Probe
3 Shaft tube
4 Handpiece
5 Distal probe end
6, 6', 6" Probe casing
7 First electrical conductor
8 Second electrical conductor
9 Electrode head
10 First pole of 9
11 Second pole of 9
12 First side face of 7
13 Second side face of 7
14 Strand of 8
15 Wire of 14
16 Handle of 4
17 Distal shaft tube end
18 Inner radius of 7, small
19 Inner radius of 8, large
20 Ring-shaped wall of 6
21 Insulating casing of 7
22 Separator wall of 6'
23 First chamber of 6'
24 Second chamber of 6'
25 Channel of 6"
26 Channel of 6"
27 Intermediate air space of 6"

What is claimed is:

1. A probe applicator (1) comprising: a substantially rigid shaft tube (3), a bipolar electrosurgical probe (2) longitudinally displaceable in the shaft tube (3), and a hand piece (4) configured to generate relative longitudinal displacement between the shaft tube (3) and the bipolar electrosurgical probe (2), the bipolar electrosurgical probe (2) having a distal end (5) and having a flexible probe casing with at least one longitudinal chamber therein, first and second electrical conductors (7, 8) in the at least one longitudinal chamber, at least part of the first electrical conductor (7) in proximity to the distal end (5) of the bipolar electrosurgical probe (2) defining a flat conductor section with opposite parallel first and second flat side faces (12, 13), and the second electrical conductor (8) being a substantially round flexible wire cable formed from plural strands, the second electrical conductor (8) being opposed to and parallel to the second flat face (13) of the first electrical conductor (7), the first electrical conductor (7) having a directionally curved pre-tensioning so that the first electrical conductor (7) is biased into a curved configuration in which one of the first and second flat side faces (12, 13) is radially outward of the other of the first and second flat side faces (12, 13) and so that the second electrical conductor (8) is spaced radially from the first electrical conductor (7), a bipolar electrode head (9) connected to ends of the first and second electrical conductors (7, 8) at the distal end (5) of the bipolar electrosurgical probe (2) and configured to close off the at least one longitudinal chamber of the probe casing, wherein, the pre-tensioning of the first electrical conductor (7) bends the distal end (5) of the bipolar electrosurgical probe (2) into a predetermined bent position when the shaft tube (3) is retracted relative to the distal end (5) of the bipolar electrosurgical probe (2), and a movement of the shaft tube (3) to an extended position surrounding the distal end (5) of the bipolar electrosurgical probe (2) tensions the first electrical conductor (7) into a substantially linear condition, thereby straightening the flexible probe casing and the flexible second electrical conductor (8).

2. The probe applicator of claim 1, wherein each of the plural strands of the flexible wire cable that comprises the second electrical conductor (8) has a plurality of wires (15).

3. The probe applicator of claim 2, wherein the flexible wire cable comprises an odd number of strands (14), each of which has an odd number of wires (15).

4. The probe applicator of claim 1, wherein the probe casing has a cross-section that is ring-shaped and wherein at least one of the first and second electrical conductors (7, 8) has an insulating cover (21).

5. The probe applicator of claim 1, wherein the at least one longitudinal chamber of the probe casing has an internal cross-section with a narrowed contour in a middle section in which the first and second electrical conductors are arranged at a distance from one another.

6. The probe applicator of claim 1, wherein the probe casing has a lumen with a separator wall (22) that divides the lumen of the probe casing into first and second separate chambers (23, 24), the first and second electrical conductors (7, 8) being arranged respectively in the first and second chambers (23, 24).

7. The probe applicator of claim 1, wherein the probe casing is made of an electrically insulating plastic.

8. The probe applicator of claim 1, wherein the first electrical conductor (7) is a rolled metal material.

9. The probe applicator of claim 1, wherein the first electrical conductor (7) is disposed with respect to the second electrical conductor (8) to be on an inner circumferential side of a curve formed by the directionally curved pre-tensioning of the first electrical conductor (7), while the second electrical conductor (8) is disposed to be on an outer circumferential side of the curve formed by the directionally curved pre-tensioning of the first electrical conductor (7).

* * * * *